US008092417B2

(12) United States Patent
Kim

(10) Patent No.: US 8,092,417 B2
(45) Date of Patent: Jan. 10, 2012

(54) DEVICE FOR REGULATING FLOW RATE

(76) Inventor: Yong-Nyun Kim, Seoul (KR)

( * ) Notice: Subject to any disclaimer, the term of this patent is extended or adjusted under 35 U.S.C. 154(b) by 1325 days.

(21) Appl. No.: 11/568,292

(22) PCT Filed: May 3, 2005

(86) PCT No.: PCT/KR2005/001283
§ 371 (c)(1),
(2), (4) Date: Oct. 25, 2006

(87) PCT Pub. No.: WO2005/105183
PCT Pub. Date: Nov. 10, 2005

(65) Prior Publication Data
US 2007/0215637 A1 Sep. 20, 2007

(30) Foreign Application Priority Data
May 3, 2004 (KR) .................. 10-2004-0031159

(51) Int. Cl.
A61N 1/30 (2006.01)
B67D 7/30 (2010.01)
G01F 11/00 (2006.01)

(52) U.S. Cl. .......................... 604/19; 222/20
(58) Field of Classification Search ............. 604/246, 604/248, 254, 32
See application file for complete search history.

(56) References Cited

U.S. PATENT DOCUMENTS
4,781,698 A 11/1988 Parren
5,033,714 A 7/1991 Winchell et al.
5,499,968 A * 3/1996 Milijasevic et al. ........... 604/30
6,213,986 B1 * 4/2001 Darling, Jr. .................. 604/248

FOREIGN PATENT DOCUMENTS
EP 0 378 141 A2 7/1990
JP 59-207160 A 11/1984
JP 5506163 A 9/1993
KR 1999-39269 U 11/1999
WO 9113641 A1 9/1991

OTHER PUBLICATIONS

Australian Government, IP Australia, Office Action issued Apr. 16, 2008 in patent application No. 2005237922 in English.

* cited by examiner

Primary Examiner — Nicholas Lucchesi
Assistant Examiner — Weng Lee
(74) Attorney, Agent, or Firm — Sughrue Mion, PLLC

(57) ABSTRACT

The present invention relates to a device for injecting a liquid medicine such as a Ringer's solution, and more particularly, to a device for regulating the amount of liquid medicine to be injected. According to the present invention, there is provided with a device for regulating the flow rate of a liquid medicine on a flow path of the liquid medicine, comprising an inflow passage for allowing the liquid medicine to be introduced therethrough; a discharge passage for allowing the liquid medicine to be discharged therethrough; a space for storing the liquid medicine introduced through the inflow passage therein; a capillary unit placed between the space and the discharge passage and having at least two capillaries and a plurality of outlets formed on the side of the discharge passage to correspond to the respective capillaries; and a discharge amount regulating valve that is placed between the capillary unit and the discharge passage and is movable to change the number of capillaries communicating with the discharge passage.

15 Claims, 9 Drawing Sheets

DEVICE FOR REGULATING FLOW RATE

TECHNICAL FIELD

The present invention relates to a device for injecting a liquid medicine such as a Ringer's solution, and more particularly, to a device for regulating the amount of liquid medicine to be injected.

BACKGROUND ART

Generally, to supplement necessary nutrients such as glucose to a patient suffering from suppressed digestive functions, a liquid medicine stored in a Ringer bottle or the like is injected into a blood vessel of the patient. When it is necessary to inject a liquid medicine such as a special injection medicine, including an anti-cancer medicine or an antibiotic, to a patient or the like, the desired amount thereof should be injected consistently and continuously depending on a patient's condition. If the amount of special injection medicine necessary for a patient is not consistently and continuously injected, there is a risk of the occurrence of shock.

A device for injecting a Ringer's solution comprises a bottle (or pack) with a liquid medicine stored therein; a hose connected to a lower end of the bottle; a member for checking the flow rate of a liquid medicine, which is installed on the hose to enable the flow rate of the liquid medicine to be viewed by the naked eye; a syringe needle installed at a leading end of the hose to pierce a blood vessel of a patient; and a regulator installed between the flow rate checking member and the syringe needle to regulate the flow rate of the liquid medicine flowing toward a syringe by adjusting the cross section of the hose. In the liquid medicine injecting device constructed as above, a nurse pierces the syringe needle into the blood vessel of the patient and adjusts the regulator to regulate the amount of liquid medicine flowing to the hose, so that necessary nutrients can be supplied to the patient.

In a conventional regulator, the regulator is generally rotated upward or downward to change the cross section of the hose, thereby regulating the amount of liquid medicine flowing to the syringe needle. However, the conventional regulator has a problem in that it is difficult to finely regulate the flow rate of liquid medicine.

DISCLOSURE

Technical Problem

An object of the invention is to provide a device for finely regulating the flow rate of a liquid medicine such as a Ringer's solution.

Technical Solution

According to an aspect of the present invention, there is provided a device for regulating the flow rate of a liquid medicine on a flow path of the liquid medicine, comprising an inflow passage for allowing the liquid medicine to be introduced therethrough; a discharge passage for allowing the liquid medicine to be discharged therethrough; a space for storing the liquid medicine introduced through the inflow passage therein; a liquid medicine passage unit that is placed between the space and the discharge passage and has at least two liquid medicine flow passages to allow the liquid medicine to flow therethrough, and a plurality of outlets formed on the side of the discharge passage to correspond to the respective liquid medicine flow passages; and a discharge amount regulating valve that is placed between the liquid medicine passage unit and the discharge passage and is movable to change the number of liquid medicine flow passages of the liquid medicine passage unit that communicate with the discharge passage.

Preferably, the liquid medicine flow passages are capillaries, and the liquid medicine passage unit comprises a capillary unit including the capillaries. However, the present invention is not limited thereto but may comprise any component with a passage through which a fluid such as a liquid medicine can flow. For example, a tube, a silicone hole and/or a plastic hole may be used as the liquid medicine flow passage. The silicone hole or plastic hole may be formed by longitudinally perforating a silicone or plastic material using a laser or other perforating means. It is preferred that the aforementioned examples of the liquid medicine flow passage allow a fluid such as a liquid medicine to flow therethrough at a predetermined speed.

The discharge amount regulating valve may be rotatable about a rotation axis and may change the number of liquid medicine flow passages, e.g., the number of capillaries, communicating with the discharge passage by means of the rotational movement thereof.

The discharge amount regulating valve may further comprise a rotary member rotatable about the rotation axis.

The rotary member may have at least a portion taking the shape of a body of revolution about the rotation axis, and an outer surface of the portion of the rotary member may be formed with a guide slot caused to communicate with the discharge passage by the rotation of the rotary member and a plurality of branched slots branched from the guide slot and adapted to communicate with the outlets of the liquid medicine passage unit, e.g., capillary unit.

The outlets of the liquid medicine passage unit, e.g., capillary unit, may be arranged equidistantly in a circumferential direction, and the branched slots of the rotary member may be arranged equidistantly in a circumferential direction.

The flow rate regulating device may further comprise an inlet for allowing the liquid medicine to flow into the space therethrough, and an inflow amount regulating valve for regulating the amount of liquid medicine introduced through the inlet according to the amount of liquid medicine stored in the space.

The inflow amount regulating valve may comprise at least one float vertically movable according to the level of the liquid medicine stored in the space, and a regulating member that is connected to the float to vertically move and restricts the amount of liquid medicine introduced through the inlet when the regulating member abuts the inlet.

The flow rate regulating device may further comprise a connection passage that has an upper end provided with the inlet and a lower end provided with an outlet communicating with the space and is larger than the inlet and the outlet. The regulating member may be accommodated in the connection passage. If the space is divided into at least two sub spaces, at least two regulating members and connection passages may be provided.

A bottom surface of the regulating member or a lower end of the connection passage may be provided with a lower protrusion for defining a gap between the bottom surface of the regulating member and the lower end of the connection passage to prevent the outlet of the connection passage from being closed.

Optionally, a top surface of the regulating member or an upper end of the connection passage may be provided with an upper protrusion for defining a gap between the top surface of the regulating member and the upper end of the connection passage to prevent the inlet of the connection passage from being closed.

The upper and lower protrusions may be formed such that a smaller amount of liquid medicine is introduced when the regulating member abuts the upper end of the connection passage.

The lower end of the connection passage provided with the outlet may become narrower downward.

The top surface of the regulating member may be configured to be narrower upward.

The flow rate regulating device may further comprise an additional space having an upper portion connected to the inflow passage and a lower portion connected to the connection passage.

The additional space may be constructed to enable checking that the liquid medicine drops from a Ringer bottle with the liquid medicine stored therein.

According to another aspect of the present invention, there is provided a device for regulating the flow rate of a liquid medicine, comprising a liquid medicine passage unit having a plurality of liquid medicine flow passages on a flow path of the liquid medicine; and a discharge amount regulating valve selectively communicating with a plurality of outlets of the liquid medicine passage unit to change the number of liquid medicine flow passages for allowing the liquid medicine to flow out therethrough from the liquid medicine passage unit.

Preferably, the liquid medicine flow passages are capillaries, and the liquid medicine passage unit comprises a capillary unit including the capillaries. However, the present invention is not limited thereto but may comprise any component with a passage through which a fluid such as a liquid medicine can flow. For example, a tube, a silicone hole and/or a plastic hole may be used as the liquid medicine flow passage. The silicone hole or plastic hole may be formed by longitudinally perforating a silicone or plastic material using a laser or other perforating means. It is preferred that the aforementioned examples of the liquid medicine flow passage allow a fluid such as a liquid medicine to flow therethrough at a predetermined speed.

The discharge amount regulating valve may be rotatable about a rotation axis and may change the number of liquid medicine flow passages, e.g., the number of capillaries, for allowing the liquid medicine to flow out therethrough by means of the rotational movement thereof.

The discharge amount regulating valve may further comprise a rotary member rotatable about the rotation axis.

The rotary member may have at least a portion taking the shape of a body of revolution about the rotation axis, and an outer surface of the portion of the rotary member may be formed with a guide slot for allowing the liquid medicine to flow out therethrough by the rotation of the rotary member and a plurality of branched slots branched from the guide slot and adapted to communicate with the outlets of the liquid medicine passage unit, e.g., capillary unit.

The outlets of the liquid medicine passage unit, e.g., capillary unit, may be arranged equidistantly in a circumferential direction, and the branched slots of the rotary member may be arranged equidistantly in a circumferential direction.

Advantageous Effects

According to the constitution of the present invention, the aforementioned object of the present invention can be fully achieved. Specifically, among a plurality of parallel disposed, liquid medicine flow passages such as capillaries through which a liquid medicine flows, the number of liquid medicine flow passages, e.g., the number of capillaries, communicating with a discharge passage is controlled so that the amount of liquid medicine to be discharged can be finely regulated. Further, since a constant amount of liquid medicine is stored in a storage space, pressure can be maintained consistently so that a constant amount of liquid medicine can be supplied to a patient.

Further, in an additional space, it is possible to check that a liquid medicine drops from a Ringer bottle with the liquid medicine stored therein. Thus, the residual amount of liquid medicine can be easily checked and a medical team can easily determine when the Ringer bottle should be exchanged.

BRIEF DESCRIPTION OF THE DRAWINGS

The above and other objects and features of the present invention will become apparent to those skilled in the art from the following description of preferred embodiments given in conjunction with the accompanying drawings, in which.

BEST MODE FOR CARRYING OUT THE INVENTION

Figure 1:
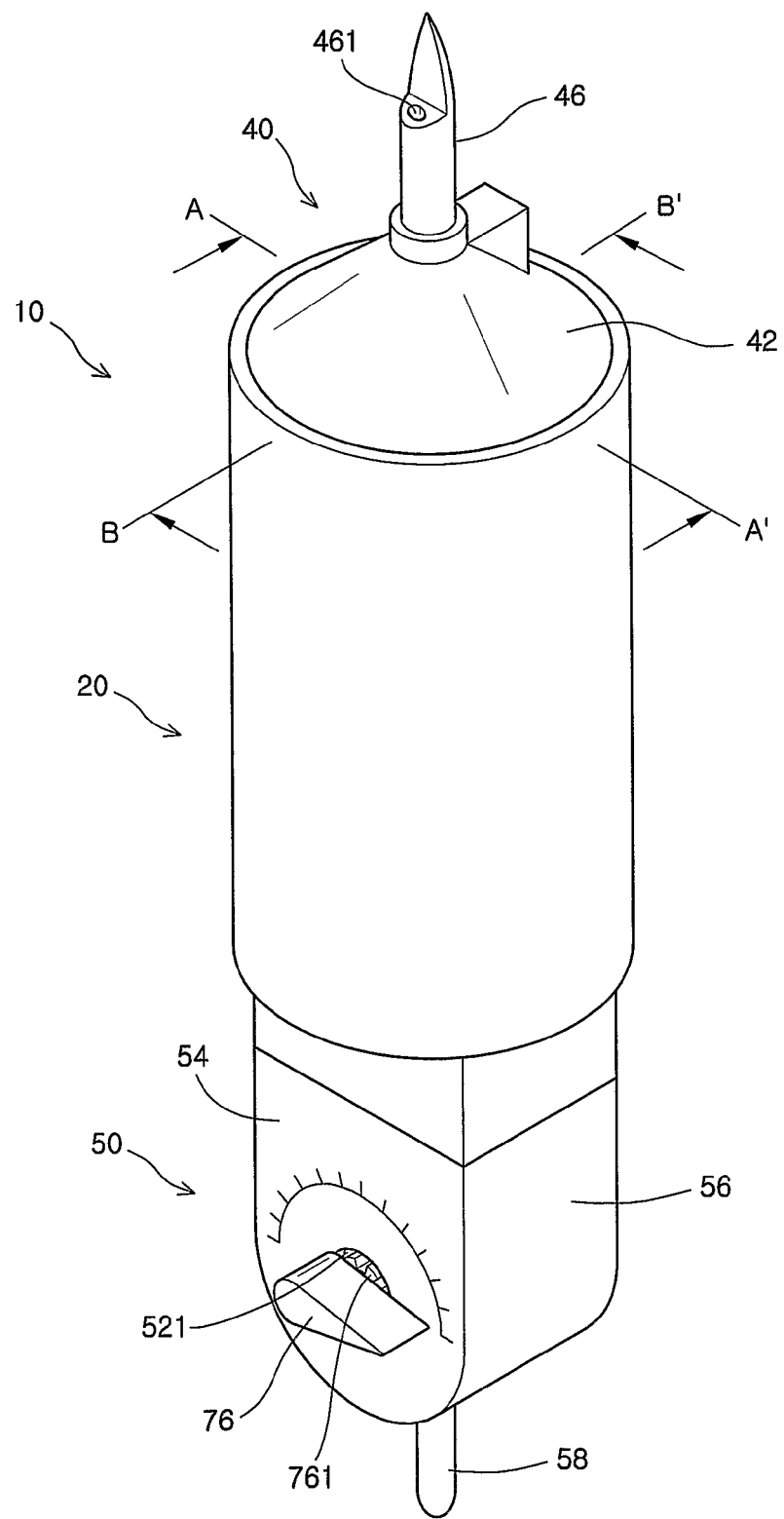
FIG. 1 is a perspective view of a device for regulating the flow rate of a liquid medicine according to an embodiment of the present invention.
Figure 2:
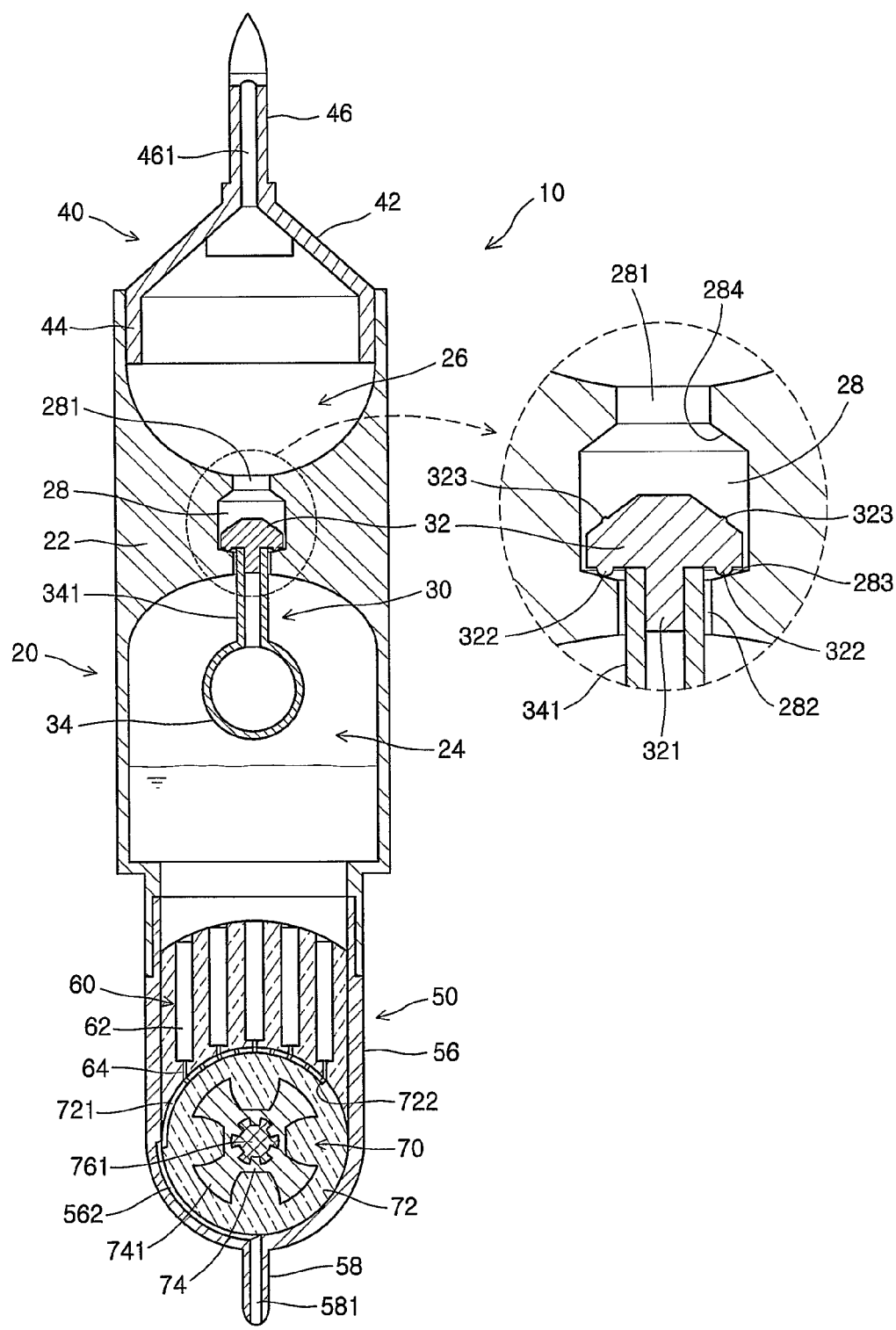
FIG. 2 is a sectional view of the flow rate regulating device of FIG. 1, taken along line A-A' to show the interior of the flow rate regulating device.
Figure 3:
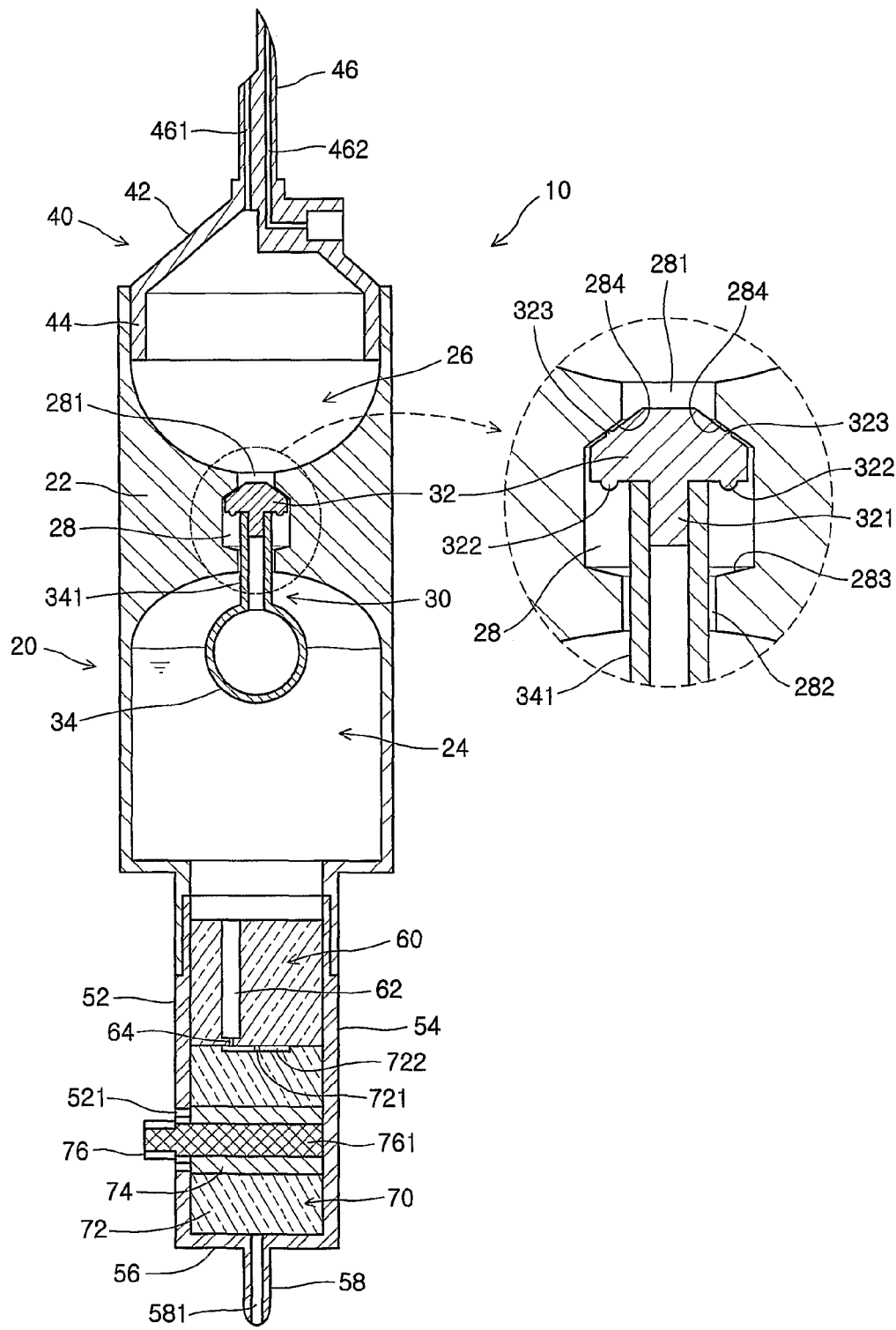
FIG. 3 is a sectional view of the flow rate regulating device of FIG. 1, taken along line B-B' to show the interior of the flow rate regulating device.

Referring to FIGS. 1 to 3, a device for regulating the flow rate of a liquid medicine 10 according to an embodiment of the present invention comprises a body 20, a valve 30, an inflow-side coupling member 40, a discharge-side coupling member 50, a liquid medicine passage unit provided with a plurality of liquid medicine flow passages, e.g., a capillary unit 60, and a control unit 70.

The body 20 of the flow rate regulating device 10 is a vertically extending cylindrical member of which a lower portion is reduced into a rectangle and slightly extends. Upper and lower ends of the body 20 are open and the inflow-side coupling member 40 and the discharge-side coupling member 50 are fitted into and coupled to the open upper and lower ends of the body, respectively. A separation wall 22 is provided within the body 20. The interior of the body 20 is divided into a lower first space 24 and an upper second space 26 by the separation wall 22. The first space 24 is a space for storing a liquid medicine and the second space 26 is a space for use in checking that the liquid medicine drops from a Ringer bottle 100 (shown in FIG. 6). The first and second spaces 24 and 26 communicate with the openings of the lower and upper ends of the body 20. The separation wall 22 is formed concavely such that its thickness is reduced toward the center thereof. The center of the separation wall 22 is provided with a vertically extending passage 28 for connecting the first and second spaces 24 and 26 to each other. An upper end of the passage 28 is provided with an inlet 281 through which the liquid medicine is introduced from the second space 26 into the passage 28, and a lower end of the passage 28 is provided with an outlet 282 through which the liquid medicine flows from the passage 28 to the first space 24. Since the outlet 282 is formed to be narrower than the passage 28, an end of the passage 28 on the side of the outlet 282 is provided with a step 283 by which a regulating member 32 of the valve 30 to be described later is caught. The step 283 slightly descends toward the center of the body. This is to allow the liquid medicine to smoothly flow into the first space 24. The inlet 281 is also formed to be narrower than the passage 28. An end of the passage 28 on the side of the inlet 281 is provided with a conically inclined surface 284 that becomes narrower toward the inlet 281 (i.e., wider toward a downstream side). This shape is determined to conform to the shape of the regulating member 32 of the valve 30 to be described later. When the regulating member 32 comes into close contact with the inclined surface 284, only a small amount of liquid medicine contained in the second space 26 can flow into the passage 28 through the inlet 281.

Referring to FIGS. 2 and 3, the valve 30 comprises the regulating member 32 that is accommodated in the passage 28 of the separation wall 22, and a float 34 positioned in the first space 24 and connected to the regulating member 32. The regulating member 32 is a member in the form of a substantially truncated cone of which the outer diameter is smaller than that of the passage 28 but larger than those of the inlet 281 and the outlet 282 connected to the passage 28. A top surface of the regulating member 32 is inclined to be narrower upward. This is to allow the introduced liquid medicine to smoothly move toward the periphery of the passage 28. The inclined portion is optionally provided with a plurality of small upper protrusions 323 arranged circumferentially. Although FIGS. 2 and 3 show that the upper protrusions 323 are provided in the present invention, the present invention is not limited thereto. If the upper inclined surface of the regulating member 32 is brought into contact with the inclined surface 284 at the upper end of the passage 28 while their shapes are substantially coincident with each other without upper protrusions, the flow of the liquid medicine from the second space 26 to the first space 24 is restricted.

In the case where the regulating member 32 has the upper protrusions 323, if the upper protrusions 323 are in contact with the inclined surface 284 at the upper end of the passage 28, a small passage is formed between the regulating member 32 and the inclined surface 284 at the upper end of the passage 28 so that a small amount of liquid medicine can be introduced through the inlet 281. The upper protrusions 323 are formed to be smaller than lower protrusions 322 to be described later. This is to allow a smaller amount of liquid medicine to be introduced when the regulating member 32 is in contact with the upper end of the passage 28. A protruding, coupling post 321 is provided at the center of a bottom surface of the regulating member 32. The coupling post 321 is fitted into and coupled to an extension tube 341 extending from the float 34. The periphery of the bottom surface of the regulating member 32 is provided with a plurality of lower protrusions 322. The lower protrusions 322 are seated on the step 283 at the lower end of the passage 28, thereby preventing the outlet 282 from being closed by the bottom surface of the regulating member 32. Although the present invention has been described in connection with this embodiment in which the regulating member 32 has the upper and lower protrusions 323 and 322, the present invention is not limited thereto. The same effects can be obtained by forming such protrusions on the inclined surface 284 and the step 283 at the upper and lower ends of the passage 28, respectively. The float 34 takes the shape of a hollow sphere and floats on the liquid medicine stored in the first space 24. The elongated extension tube 341 extending upward is provided on an upper portion of the float 34. The extension tube 341 enters the outlet 282 communicating with the passage 28 formed in the separation wall 22. The coupling post 321 of the regulating member 32 is fitted into an open upper end of the extension tube 341 so that the float 34 and the regulating member 32 are coupled to each other and move vertically together. The outer diameter of the extension tube 341 is smaller than that of the outlet 282 so that the liquid medicine can pass through the outlet 282.

Figure 6:
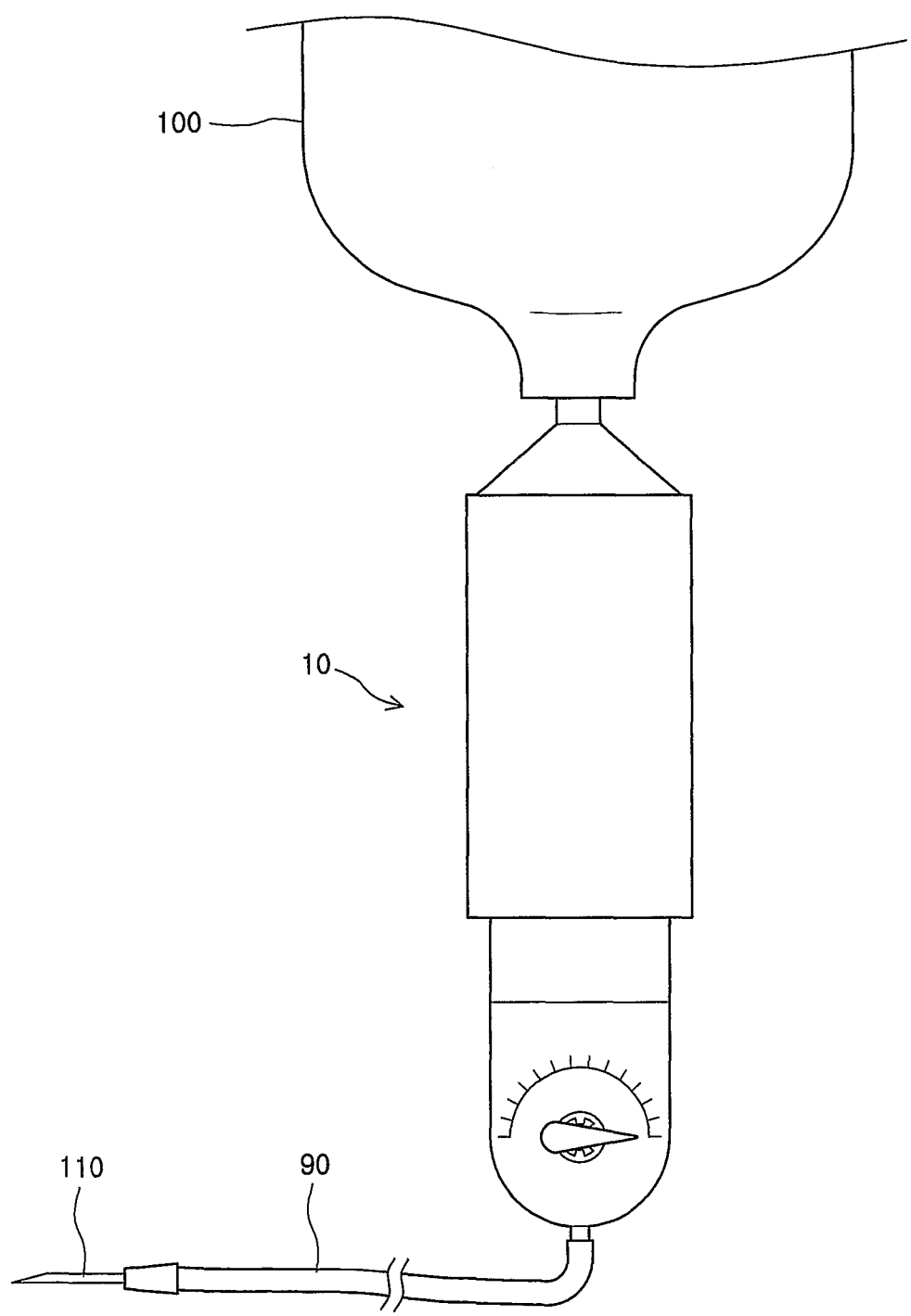
FIG. 6 is a view exemplarily showing a state where the flow rate regulating device of FIG. 1 is used.

Referring to FIGS. 1 to 3, the inflow-side coupling member 40 comprises an upper wall 42, a sidewall 44 extending downward from the upper wall 42, and an elongated extension projection 46 protruding and extending upward from a central portion of the upper wall 42. The upper wall 42 is inclined to be narrower upward. The sidewall 44 is fitted into the open upper end of the body 20 and comes into close contact with a wall surface of the body 20. The extension projection 46 is provided with a vertically extending liquid medicine inflow passage 461 and air inflow passage 462. The liquid medicine inflow passage 461 communicates with the second space 26 of the body 20, and the air inflow passage 462 communicates with the outside through the upper wall 42. An upper end of the liquid medicine inflow passage 461 is positioned at a level lower than that of an upper end of the air inflow passage 462. This is to allow air to flow into the Ringer bottle 100 so that the liquid medicine in the Ringer bottle 100 can be smoothly moved into the second space 26 of the flow rate regulating device 10 through the liquid medicine inflow passage 461, in a state where the flow rate regulating device 10 is connected to the Ringer bottle 100 as shown in FIG. 6.

Referring to FIGS. 1 to 3, the discharge-side coupling member 50 has a space for accommodating the capillary member 60 and the control unit 70 therein. To this end, the discharge-side coupling member 50 comprises first and second flat sidewalls 52 and 54 that face each other and extend vertically, and a connection wall 56 for connecting the first and second sidewalls 52 and 54 to each other. Lower edges of the first and second sidewalls 52 and 54 take the shape of a semicircle. Accordingly, the connection wall 56 is also connected roundly at a lower portion thereof. The discharge-side coupling member 50 has an open upper end that in turn is fitted into the open lower end of the body 20, thereby communicating with the first space 24. The first sidewall 52 is formed with a circular through-hole 521. The center of the through-hole 521 is generally coincident with the center of a cylindrical rotary member 72 that will be described later and is accommodated in the discharge-side coupling member 50. Tooth posts 761 connected to a knob 76 of the control unit 70 to be described later are inserted into a toothed hole 742 of an insertion member 74 through the through-hole 521. A lower end of the connection wall 56 of the discharge-side coupling member 50 is provided with an extension projection 58 protruding extending downward. A discharge passage 581 which communicates with the interior of the discharge-side coupling member 50 and through which the liquid medicine is discharged is provided within the extension projection 58. The extension projection 58 is fitted into a connection hose 90 connected to a syringe needle 110, as shown in FIG. 6.

Referring again to FIGS. 1 to 3, a discharge groove 562 communicating with the discharge passage 581 is provided in an inner wall surface of the connection wall 56. The discharge groove 562 extends circumferentially by about 90 degrees from the discharge passage 581 along the wall surface of the connection wall 56.

Figure 4:
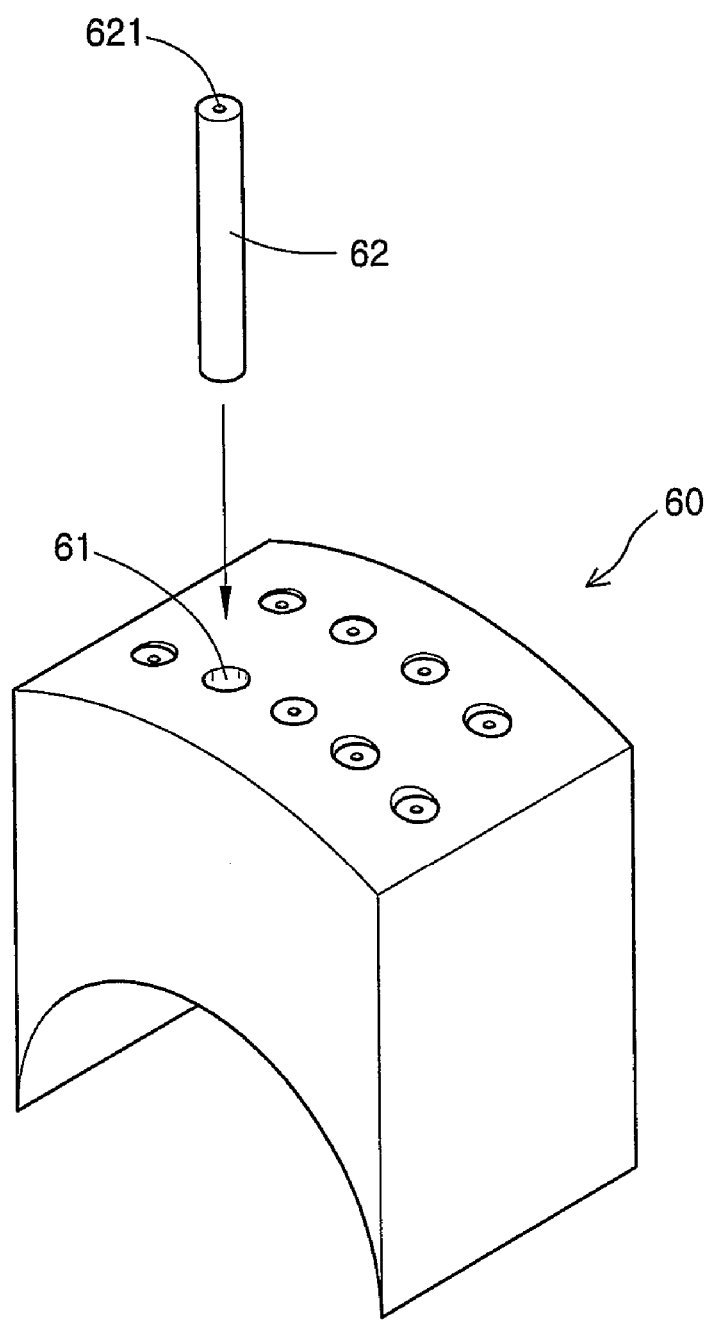
FIG. 4 is a perspective view of a capillary member shown in FIGS. 2 and 3.
Figure 5:
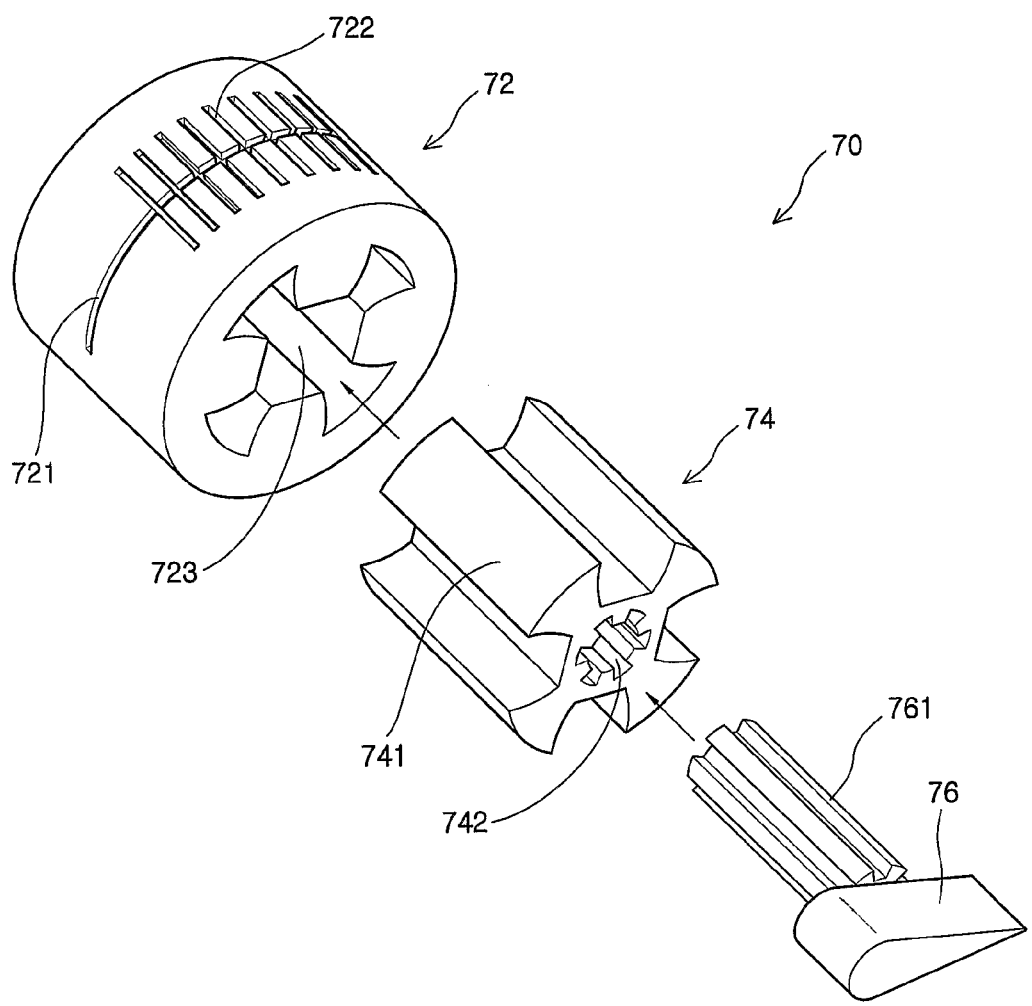
FIG. 5 is an exploded perspective view of a rotary member shown in FIGS. 1, 2 and 3.

Referring to FIGS. 2 to 4, the liquid medicine passage unit, for example, the capillary member 60, is configured to be tightly fitted into an upper portion of the discharge-side coupling member 50 and to have a concave semicircular lower surface that is to be in close contact with an outer periphery of the rotary member 72 of the control unit 70 to be described later. Although the present invention has been described by way of example in connection with the embodiment that employs the capillary member with capillaries as the liquid medicine flow passages, the present invention is not limited thereto. The liquid medicine passage unit of the present invention may comprise any component with a passage through which a fluid such as a liquid medicine can flow. For example, a tube, a silicone hole and/or a plastic hole may be used as the liquid medicine flow passage. The silicone hole or plastic hole may be formed by longitudinally perforating a silicone or plastic material using a laser or other perforating means. It is preferred that the aforementioned examples of the liquid medicine flow passage allow a fluid such as a liquid medicine to flow therethrough at a predetermined speed.

The capillary member 60 that is exemplarily shown in FIGS. 2 to 4 is provided with a plurality of vertically extending capillaries. The plurality of capillaries are provided by fitting capillary elements 62 with capillaries 621 into the capillary member 60. The capillary member 60 is provided with a plurality of insertion holes 61 into which the capillary elements 62 are tightly fitted. The bottoms of the plurality of insertion holes 61 are formed with connection passages 64 extending to the lower surface of the capillary member 60. The respective connection passages 64 are caused to communicate with branched slots 722 formed in the outer periphery of the rotary member 72 of the control unit 70 to be described later.

The plurality of capillaries 621 are arranged in two rows such that a first row has five capillaries and a second row has four capillaries. The capillaries 612 arranged in the respective rows are disposed equidistantly, and each of the capillaries arranged in the second row is disposed at a position corresponding to an intermediate position between adjacent capillaries in the first row. However, the number or arrangement of the capillaries is not limited thereto. Further, it can be readily understood by those skilled in the art that instead of the capillary elements 62, a tube, a silicone hole and/or a plastic hole can be used to allow a fluid such as a liquid medicine to flow therethrough at a predetermined speed.

Referring to FIGS. 1, 2, 3 and 5, the control unit 70 comprises the cylindrical rotary member 72, the insertion member 74 coupled to the center of the rotary member 72, and the control knob 76 connected to the insertion member 74. The outer periphery of the rotary member 72 is provided with a circumferential guide slot 721 over a portion of the outer periphery, and the plurality of branched slots 722 that are branched and extend from both sides of the guide slot 721. The guide slot 721 communicates with the discharge groove 562 of the discharge-side coupling member 50. The branched slots 722 are arranged equidistantly. The branched slots 722 are caused to communicate with, for example, the connection passages 64 of the capillary member 60. The number of branched slots is determined such that the branched slots alternately communicate with the connection passages. The center of the rotary member 72 is provided with a coupling hole 723 into which the insertion member 74 is tightly fitted. The shape and size of the coupling hole 723 are determined to conform to the insertion member 74. Although not shown, the centerline of the rotary member 72 becomes a rotation axis of the rotary member 72. Although the present invention has been described in connection with the embodiment in which the rotary member 72 takes the shape of a cylinder, the present invention is not limited thereto. It will be understood by those skilled in the art that the shape of the lower surface of the capillary member 60 can be also determined properly according to the shape of the rotary member. The configuration of the slots formed in the outer periphery of the rotary member 72 is not limited to the configuration shown in FIG. 5. For example, the configuration may comprise two branched slots extending circumferentially by a predetermined length (in this case, it generally takes the shape of a tuning fork or is Y-shaped). The two branched slots are caused to communicate with the first and second rows in the capillary member 60, respectively.

The insertion member 74 comprises a plurality of radially extending wings 741, and the toothed hole 742 formed at the center thereof. The insertion member 74 is tightly fitted into the coupling hole 723 of the rotary member 72. The tooth posts 761 connected to the control knob 76 are tightly fitted into the toothed hole 742 so that the rotation of the control knob 76 can be directly transmitted thereto. The wings 741 transmit the rotational force to the rotary member 72. The toothed hole 742 is exposed to the outside through the through-hole 521 formed in the first sidewall 52 of the discharged-side coupling member 50. The tooth posts 761 are connected to the control knob 76. The tooth posts 761 are tightly fitted into the toothed hole 742 of the insertion member 74 through the through-hole 521 formed in the first sidewall 52 of the discharge-side coupling member 50. The control knob 76 is placed outside the first sidewall 52 of the discharge-side coupling member 50. When a user grasps and rotates the control knob 76, the rotary member 72 is rotated.

Now, the operation of the embodiment of the present invention will be described in detail with reference to FIGS. 1 to 7. Referring to FIG. 6, the extension projection 46 of the inflow-side coupling member 40 of the flow rate regulating device 10 is inserted into a lower end of the Ringer bottle 100, and the connection hose 90 with the syringe needle 110 coupled thereto is fitted around the extension projection 58 of the discharge-side coupling member 50. The liquid medicine contained in the Ringer bottle 100 is introduced into the second space 26 of the body 20 through the liquid medicine inflow passage 461 provided in the extension projection 46 of the inflow-side coupling member 40. At this time, external air is introduced into the Ringer bottle 100 through the air inflow passage 462 of the extension projection 46 so that the liquid medicine can be smoothly introduced into the second space 26 of the body 20. The liquid medicine that has been introduced into the second space 26 of the body 20 is then introduced into the passage 28 of the separation wall 22 through the inlet 281 of the passage 28 in a state where the regulating member 32 of the valve 30 is lowered as shown in FIG. 2. The liquid medicine that has been introduced into the passage 28 flows down through a gap defined at an edge of the passage 28 between the wall surface of the passage 28 and the regulating member 32 and then into the first space 24 through the outlet 282. The liquid medicine that has been introduced into the first space 24 is stored in the first space 24 and the level of the liquid medicine stored in the first space 24 is raised with time.

As the level of the liquid medicine is raised, the float 34 of the valve 30 is lifted. When the first space 24 is consequently filled with the liquid medicine to a certain degree as shown in FIG. 3, the regulating member 32 of the valve 30 abuts the upper end of the passage 28 so that the amount of liquid medicine to be introduced is preferably decreased and the pressure of the liquid medicine stored in the first space 24 is maintained consistently, thereby keeping a constant amount of liquid medicine supplied to a patient.

Figure 7:
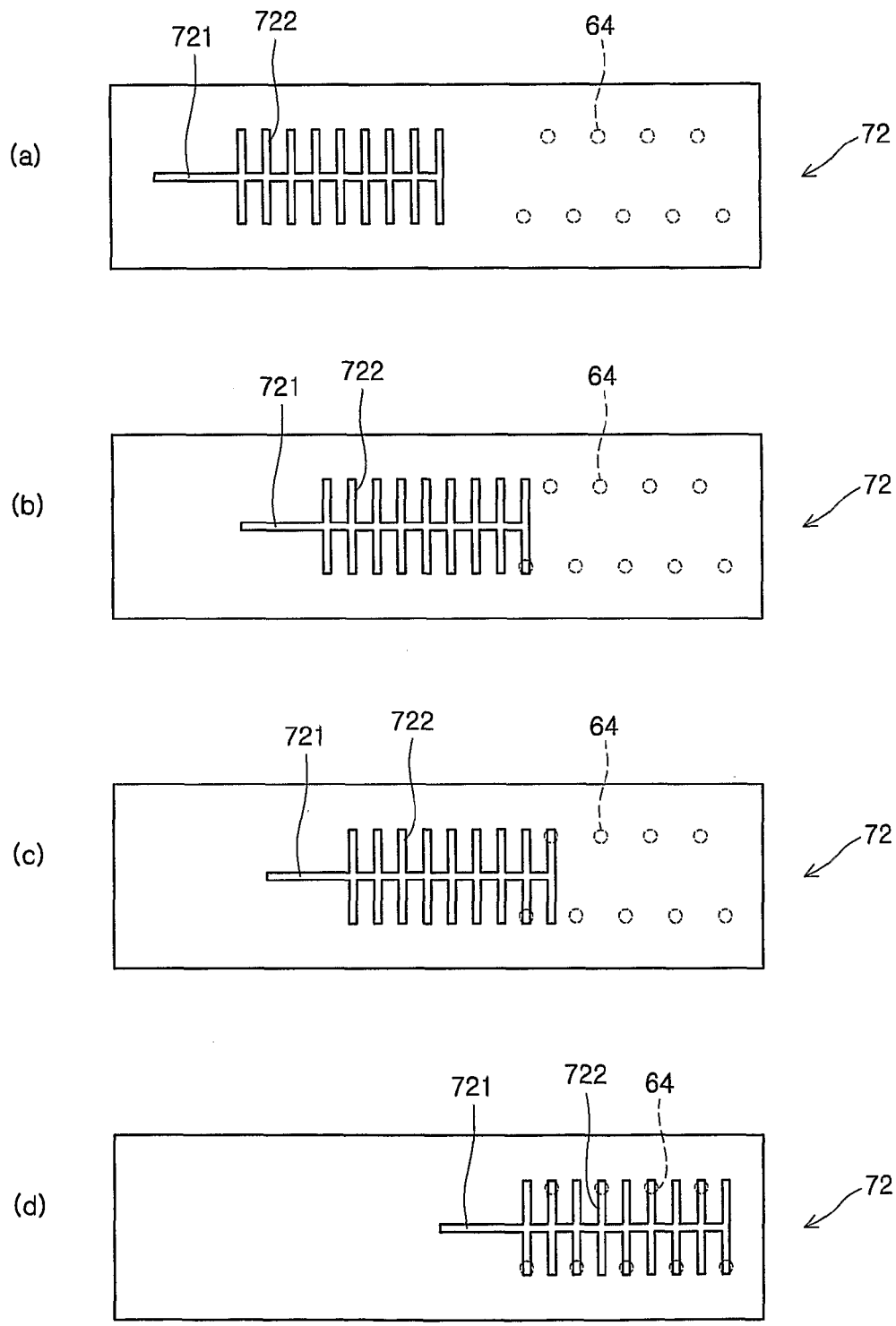
FIGS. 7 (*a*) to (*d*) are views showing the state of connection of the rotary member to connection passages of the capillary member, while an outer periphery of the rotary member of FIG. 5 is deployed.

The liquid medicine stored in the first space 24 flows downward little by little, for example, through the capillaries 621 formed in the capillary elements 62 of the capillary member 60. At this time, if the rotated state of the rotary member 72 is a state shown in FIG. 7 (a), i.e., a state where all the connection passages 64 of the capillary member 60 do not communicate with the branched slots 722 of the rotary member 72, any liquid medicine cannot be discharged to the connection hose 90. In this state, if the control knob 76 is rotated so that one of the connection passages 64 of the capillary member 60 is caused to communicate with the branched slot 722 of the rotary member 72 as shown in FIG. 7 (b), the liquid medicine is discharged through this connection passage to the connection hose 90. If the control knob 76 is slightly further rotated from this state so that two of the connection passages 64 of the capillary member 60 are caused to communicate with the branched slots 722 of the rotary member 72 as shown in FIG. 7 (c), the flow rate of the liquid medicine to be discharged to the connection hose 90 is slightly increased. The flow rate of the liquid medicine to be discharged can be finely increased by rotating the rotary member 72 stepwise in the same direction. If the rotary member 72 is further rotated so that all the connection passages 64 of the capillary member 60 are caused to communicate with the branched slots 722 of the rotary member 72 as shown in FIG. 7 (d), the flow rate of the liquid medicine to be discharged to the connection hose 90 is maximized. If the rotary member 72 is rotated in a reverse direction, the flow rate of the liquid medicine can be finely decreased stepwise.

Figure 8:
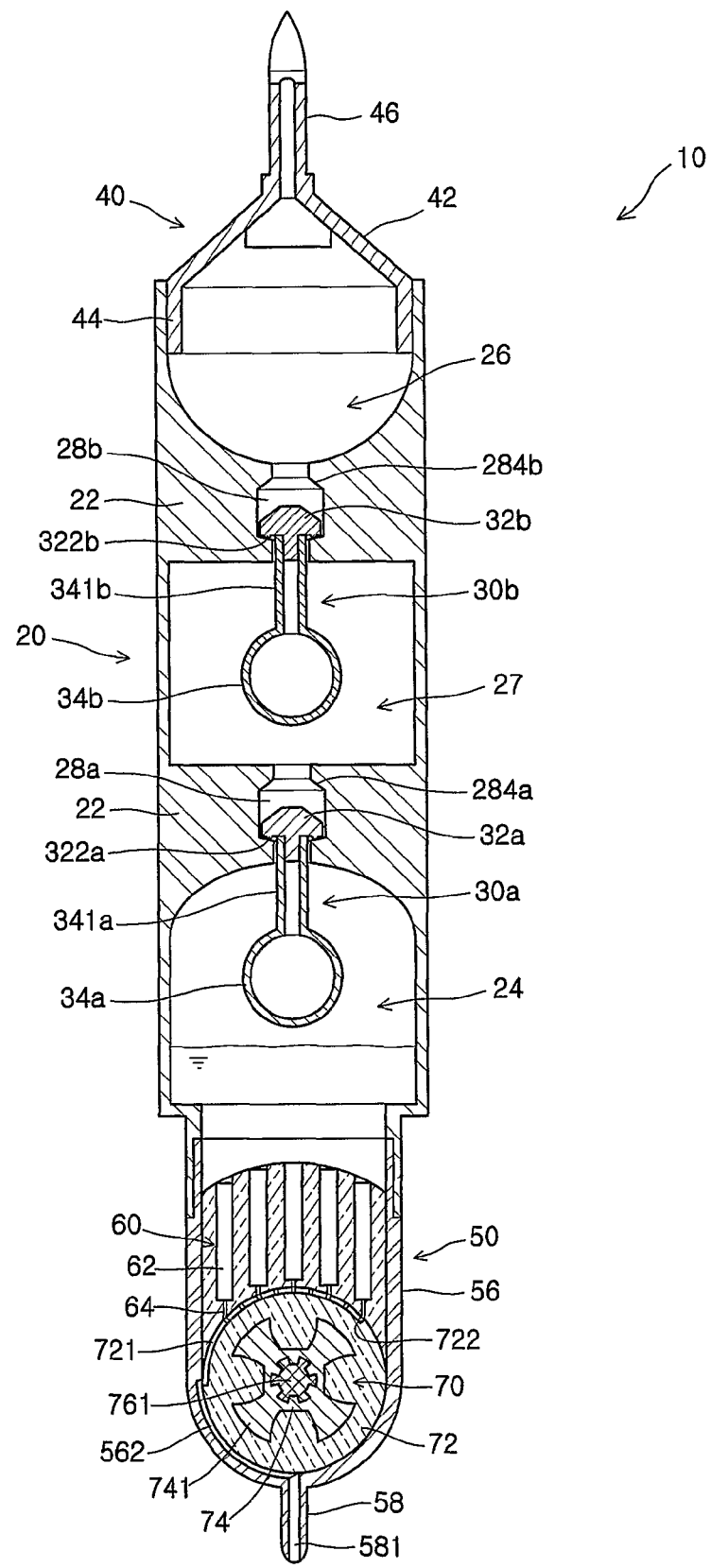
FIG. 8 is a sectional view of a device for regulating the flow rate of a liquid medicine according to another embodiment of the present invention, taken in the same direction as FIG. 1 to show the interior of the flow rate regulating device.
Figure 9:
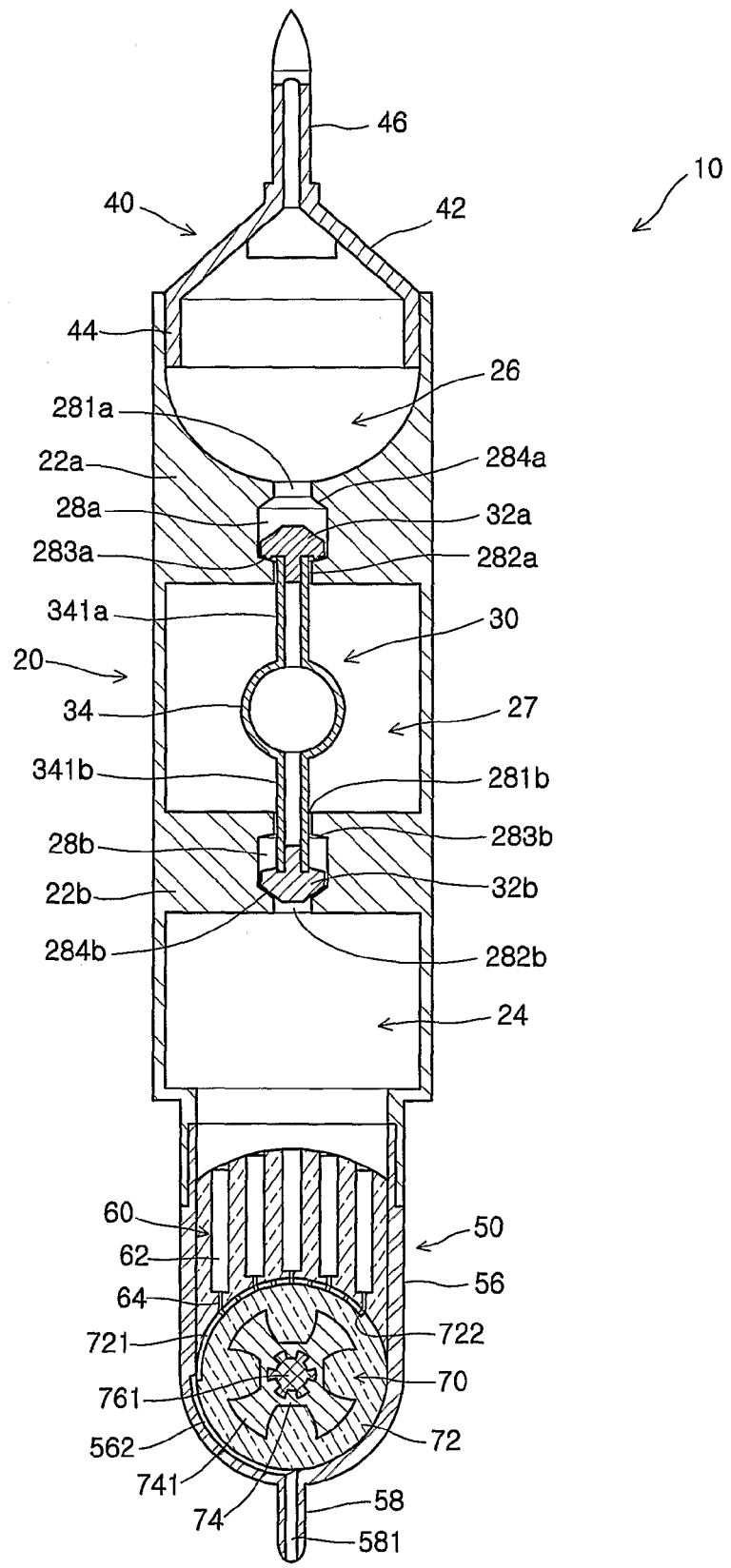
FIG. 9 is a sectional view of a device for regulating the flow rate of a liquid medicine according to a further embodiment of the present invention, taken in the same direction as FIG. 1 to show the interior of the flow rate regulating device.

FIGS. 8 and 9 show sectional views of other embodiments of the present invention. The embodiments shown in FIGS. 8 and 9 are identical to the embodiment of the present invention shown in FIGS. 2 and 3 except the structure of the inflow amount regulating valve that is placed in the body 20 and comprises the first space, the second space, the regulating member, the connection passages, the float and the like. Therefore, descriptions of identical components will be omitted, and components similar to those of the embodiment shown in FIGS. 2 and 3 will be described using identical or like reference numerals.

In the embodiment shown in FIG. 8, two separation walls 22 are provided in the body 20. The interior of the body 20 is divided into a lowermost first space 24, an uppermost second space 26 and an intermediate third space 27 by the two separation walls 22. The first space 24 is a space in which the liquid medicine is finally stored, the second space 26 is a space for use in checking that the liquid medicine drops from the Ringer bottle 100 (shown in FIG. 6). The third space 27 is positioned between the second and first spaces 26 and 24 to temporarily store the liquid medicine therein.

In this modified embodiment, the inflow amount regulating valves installed within the body 20 comprise a first inflow amount regulating valve 30a and a second inflow amount regulating valve 30b. The first inflow amount regulating valve 30a regulates the flow of the liquid medicine between the first space 24 and a first connection passage 28a, and the second inflow amount regulating valve 30b regulates the flow of the liquid medicine between the third space 27 and a second connection passage 28b. The valves 30a and 30b comprises a first regulating member 32a and a second regulating member 32b accommodated in the first and second connection passages 28a and 28b of the two separation walls 22, respectively. Further, the valves 30a and 30b comprises a first float 34a and a second float 34b that are placed in the first and third spaces 24 and 27 and connected to the first and second regulating members 32a and 32b, respectively. Although no upper protrusion is provided on inclined top surfaces of the first and second regulating members 32a and 32b in FIG. 8, a plurality of small upper protrusions may be circumferentially arranged on the inclined top surfaces of the regulating members in the same manner as the embodiment shown in FIG. 2. When the top surfaces of the first and second regulating members 32a and 32b are brought into contact with a first inclined surface 284a at an upper end of the first connection passage 28a and a second inclined surface 284b at an upper end of the second connection passage 28b, respectively while their shapes are substantially coincident with each other, the flow of liquid medicine from the second space 26 to the third space 27 and the flow of liquid medicine from the third space 27 to the first space 24 are subsequently restricted. Therefore, this modified embodiment can more finely regulate the inflow amount of liquid medicine than the previous embodiment.

The first and second regulating members 32a and 32b have coupling posts extending from the centers of bottom surfaces thereof. These coupling posts are fitted into and coupled to first and second extension tubes 341a and 341b extending from the first and second floats 34a and 34b, respectively. A plurality of lower protrusions 322a and 322b spaced apart from one another are provided on edges of the bottom surfaces of the first and second regulating members 32a and 32b, respectively. The lower protrusions 322a and 322b are seated on steps at lower ends of the first and second connection passages 28a and 28b, thereby preventing outlets from being closed by the bottom surfaces of the first and second regulating members 32a and 32b. In this modified embodiment, the sizes of the lower protrusions 322a and 322b can be changed so that the second and first inflow amount regulating valves 30b and 30a can finely regulate the flow of the liquid medicine from the second space 26 to the third space 27 and the flow of the liquid medicine from the third space 27 to the first space 24.

In a further modified embodiment shown in FIG. 9, two separation walls 22a and 22b are provided in the body 20. The interior of the body 20 is divided into a lowermost first space 24, an uppermost second space 26 and an intermediate third space 27 by the two separation walls 22a and 22b. The first space 24 is a space in which the liquid medicine is finally stored, the second space 26 is a space for use in checking that the liquid medicine drops from the Ringer bottle 100 (shown in FIG. 6). The third space 27 is positioned between the second and first spaces 26 and 24 to temporarily store the liquid medicine therein.

The center of the upper separation wall 22a is provided with a first extension passage 28a vertically extending to connect the second and third spaces 26 and 27 to each other. The center of the lower separation wall 22b is provided with a second extension passage 28b vertically extending to connect the third and first spaces 27 and 24 to each other. As shown in FIG. 9, the first and second extension passages 28a and 28b are configured to be symmetric with each other with respect to the second space 27.

An upper end of the first extension passage 28a is provided with a first inlet 281a through which the liquid medicine flows from the second space 26 to the first extension passage 28a, and a lower end of the first extension passage 28a is provided with a first outlet 282*a* through which the liquid medicine flows from the first extension passage 28*a* to the third space 27. Since the first outlet 282*a* is formed to be narrower than the first extension passage 28*a*, an end of the first extension passage 28*a* on the side of the first outlet 282*a* is provided with a first step 283*a* by which the first regulating member 32*a* of the valve 30 to be described later is caught. The first inlet 281*a* is also formed to be narrower than the first extension passage 28*a*. An end of the first extension passage 28*a* on the side of the first inlet 281*a* is provided with a first conically inclined surface 284*a* that becomes narrower toward the first inlet 281*a*.

An upper end of the second extension passage 28*b* is provided with a second inlet 281*b* through which the liquid medicine flows from the third space 27 to the second extension passage 28*b*, and a lower end of the second extension passage 28*b* is provided with a second outlet 282*b* through which the liquid medicine flows from the second extension passage 28*b* to the first space 24. The second outlet 282*b* is formed to be narrower than the second extension passage 28*b*. An end of the second extension passage 28*b* on the side of the second outlet 282*b* is provided with a second conically inclined surface 284*b* that becomes narrower toward the second outlet 282*b*. Since the second inlet 281*b* is formed to be narrower than the second extension passage 28*b*, an end of the second extension passage 28*b* on the side of the second inlet 281*b* is provided with a second step 283*b* by which the second regulating member 32*b* of the valve 30 to be described later is caught.

The valve 30 comprises the first regulating member 32*a* accommodated in the first extension passage 28*a* of the first separation wall 22*a*, the second regulating member 32*b* accommodated in the second extension passage 28*b* of the second separation wall 22*b*, and a float 34 for connecting the first and second regulating members 32*a* and 32*b* to each other such that they face each other in a symmetric manner. Since the first regulating member 32*a* is substantially identical to the regulating member 32 shown in FIGS. 2 and 3 in their constitutions, a detailed description thereof will be omitted. The second regulating member 32*b* is accommodated in the second extension passage 28*b*.

Although no upper protrusion is provided on an inclined top surface of the first regulating member 32*a* in FIG. 9, a plurality of small upper protrusions may be circumferentially arranged on the inclined top surface of the first regulating member 32*a* in the same manner as the embodiment shown in FIG. 2. When the inclined top surface of the first regulating member 32*a* is brought into contact with a first inclined surface 284*a* at an upper end of the first extension passage 28*a* while their shapes are substantially coincident with each other, and at the same time, a bottom surface of the second regulating member 32*b* is brought into contact with the second step 283*b* at an upper end of the second extension passage 28*b* while their shapes are substantially coincident with each other, the flow of the liquid medicine from the second space 26 to the third space 27 and the flow of the liquid medicine from the third space 27 to the first space 24 are restricted. At this time, a certain amount of liquid medicine, which cannot completely fill the third space 27, is temporarily stored in the third space 27. Thus, when the liquid medicine is supplied again, the liquid medicine temporarily stored in the third space 27 can be quickly supplied to the first space 24.

The first and second regulating members 32*a* and 32*b* have coupling posts extending from the centers of the bottom surfaces thereof. These coupling posts are fitted into and coupled to first and second extension tubes 341*a* and 341*b* extending from the float 34 in opposite directions. A plurality of lower protrusions spaced apart from one another are provided on an edge of the bottom surface of the first regulating member 32*a*. The lower protrusions of the first regulating member 32*a* are seated on the first step 283*a* at a lower end of the first extension passage 28*a* and the upper protrusions of the second regulating member 32*b* are seated on the second inclined surface 284*b* of the second extension passage 28*b*, thereby preventing the respective outlets from being closed by the bottom surface of the first regulating member 32*a* and the top surface of the second regulating member 32*b*. In this modified embodiment, the sizes of the lower and upper protrusions can be changed to finely regulate the flow of the liquid medicine from the second space 26 to the third space 27 and the flow of the liquid medicine from the third space 27 to the first space 24.

Although the present invention has been described in connection with the embodiments, it is not limited thereto. It can be understood by those skilled in the art that various modifications and changes can be made thereto without departing from the spirit and scope of the present invention and such modifications and changes fall within the scope of the present invention.

The invention claimed is:

1. A device for regulating the flow rate of a liquid medicine on a flow path of the liquid medicine, comprising:
   an inflow passage for allowing the liquid medicine to be introduced therethrough;
   a discharge passage for allowing the liquid medicine to be discharged therethrough;
   a space for storing the liquid medicine introduced through the inflow passage;
   a liquid medicine passage unit placed between the space and the discharge passage and having a plurality of liquid medicine flow passages to allow the liquid medicine to flow therethrough, and a plurality of outlets formed at the end of the respective liquid medicine flow passages toward the discharge passage to correspond to the respective liquid medicine flow passages, wherein the plurality of liquid medicine flow passages are arranged to form a first row of a plurality of liquid medicine flow passages and a second row of a plurality of liquid medicine flow passages, wherein the plurality of liquid medicine flow passages of the first row and of the second row are disposed equidistantly in a circumferential direction, and wherein each of the liquid medicine flow passages of the second row is disposed at a position corresponding to a middle position between the adjacent liquid medicine flow passages of the first row; and
   a discharge amount regulating valve placed between the liquid medicine passage unit and the discharge passage, the discharge amount regulating valve being rotatable about a rotation axis to change the number of liquid medicine flow passages of the liquid medicine passage unit that communicate with the discharge passage;
   wherein the discharge amount regulating valve comprises a rotary member rotatable about the rotation axis, the rotary member having at least a portion taking the shape of a body of revolution about the rotation axis, and wherein an outer surface of the portion of the rotary member is formed with a guide slot caused to communicate with the discharge passage by a rotation of the rotary member and a plurality of branched slots branched and extended from both sides of the guide slot and adapted to communicate with the outlets of the liquid medicine passage unit;
   wherein the outlets of the liquid medicine passage unit are arranged equidistantly in a circumferential direction, and the branched slots extended from both sides of the guide slot of the rotary member are arranged equidistantly in a circumferential direction; and wherein when the discharge amount regulating valve is rotated by a rotational movement of the rotary member, the respective liquid medicine flow passages of the first row and the second row alternately communicate with the branched slots of the rotary member via the outlets of the liquid medicine passage unit so as to change the number of the branched slots of the rotary member communicating with the liquid medicine flow passages via the outlets of the liquid medicine passage unit, and finally to change the number of liquid medicine flow passages communicating with the discharge passage.

2. The device as claimed in claim 1, wherein the liquid medicine flow passages are capillaries, and the liquid medicine passage unit comprises a capillary unit including the capillaries.

3. The device as claimed in claim 1, further comprising an inlet for allowing the liquid medicine to flow into the space therethrough, and an inflow amount regulating valve for regulating the amount of liquid medicine introduced through the inlet according to the amount of liquid medicine stored in the space.

4. The device as claimed in claim 3, wherein the inflow amount regulating valve comprises at least one float vertically movable according to the level of the liquid medicine stored in the space, and a regulating member connected to the float to vertically move, the regulating member restricting the amount of liquid medicine introduced through the inlet when the regulating member abuts the inlet.

5. The device as claimed in claim 4, further comprising a connection passage having an upper end located at the inlet for allowing the liquid medicine to flow into the space and a lower end located at an outlet communicating with the space, the connection passage being larger than the inlet and the outlet communicating with the space, the regulating member being accommodated in the connection passage.

6. The device as claimed in claim 5, wherein if the space is divided into at least two sub spaces, at least two regulating members and connection passages are provided.

7. The device as claimed in claim 5, wherein a bottom surface of the regulating member or a lower end of the connection passage is provided with a lower protrusion for defining a gap between the bottom surface of the regulating member and the lower end of the connection passage to prevent the outlet of the connection passage from being closed.

8. The device as claimed in claim 7, wherein a top surface of the regulating member or an upper end of the connection passage is provided with an upper protrusion for defining a gap between the top surface of the regulating member and the upper end of the connection passage to prevent the inlet of the connection passage from being closed.

9. The device as claimed in claim 8, wherein the upper and lower protrusions are formed such that a smaller amount of liquid medicine is introduced when the regulating member abuts the upper end of the connection passage.

10. The device as claimed in claim 5, wherein the lower end of the connection passage located at the outlet communicating with the space becomes narrower downward.

11. The device as claimed in claim 10, wherein the top surface of the regulating member is configured to be narrower upward.

12. The device as claimed in claim 5, further comprising an additional space having an upper portion connected to the inflow passage and a lower portion connected to the connection passage.

13. The device as claimed in claim 12, wherein the additional space is constructed to enable checking that the liquid medicine drops from a Ringer bottle with the liquid medicine stored therein.

14. A device for regulating the flow rate of a liquid medicine, comprising:
a liquid medicine passage unit having a plurality of liquid medicine flow passages on a flow path of the liquid medicine, and a plurality of outlets formed at the end of the respective liquid medicine flow passages to correspond to the respective liquid medicine flow passages, wherein the plurality of liquid medicine flow passages are arranged to form a first row of a plurality of liquid medicine flow passages and a second row of a plurality of liquid medicine flow passages, wherein the plurality of liquid medicine flow passages of the first row and of the second row are disposed equidistantly in a circumferential direction, and wherein each of the liquid medicine flow passages of the second row is disposed at a position corresponding to a middle position between the adjacent liquid medicine flow passages of the first row; and
a discharge amount regulating valve selectively communicating with a plurality of outlets of the liquid medicine passage unit to change the number of liquid medicine flow passages for allowing the liquid medicine to flow out therethrough from the liquid medicine passage unit;
wherein the discharge amount regulating valve comprises a rotary member rotatable about a rotation axis, the rotary member having at least a portion taking the shape of a body of revolution about the rotation axis, and wherein an outer surface of the portion of the rotary member is formed with a guide slot for allowing the liquid medicine to flow out therethrough by a rotation of the rotary member and a plurality of branched slots branched and extended from both sides of the guide slot and adapted to communicate with the outlets of the liquid medicine passage unit;
wherein the outlets of the liquid medicine passage unit are arranged equidistantly in a circumferential direction, and the branched slots extended from both sides of the guide slot of the rotary member are arranged equidistantly in a circumferential direction; and
wherein when the discharge amount regulating valve is rotated by a rotational movement of the rotary member, the respective liquid medicine flow passages of the first row and the second row alternately communicate with the branched slots of the rotary member via the outlets of the liquid medicine passage unit so as to change the number of the branched slots of the rotary member communicating with the liquid medicine flow passages via the outlets of the liquid medicine passage unit, and finally to change the number of liquid medicine flow passages communicating with the guide slot for allowing the liquid medicine to flow out therethrough.

15. The device as claimed in claim 14, wherein the liquid medicine flow passages are capillaries, and the liquid medicine passage unit comprises a capillary unit including the capillaries.

* * * * *